US007871571B2

(12) United States Patent
Parker et al.

(10) Patent No.: US 7,871,571 B2
(45) Date of Patent: Jan. 18, 2011

(54) BIOMOLECULE ANALYZING SYSTEM

(76) Inventors: John A. Parker, 3330 Seaman Ave., El Monte, CA (US) 91733; Mike VanDeMortel, 5110 Webb Pl., Yorba Linda, CA (US) 92886

(*) Notice: Subject to any disclaimer, the term of this patent is extended or adjusted under 35 U.S.C. 154(b) by 538 days.

(21) Appl. No.: 11/977,679

(22) Filed: Oct. 25, 2007

(65) Prior Publication Data

US 2009/0111174 A1 Apr. 30, 2009

(51) Int. Cl.
*G01N 27/00* (2006.01)
*G01N 15/06* (2006.01)
*G01N 33/00* (2006.01)
*G01N 33/48* (2006.01)

(52) U.S. Cl. ..................... 422/82.01; 422/68.1; 422/50; 422/55; 422/82.05; 977/902; 977/920; 977/924; 977/953; 977/957; 977/958

(58) Field of Classification Search .............. 422/82.01; 977/902, 920, 924, 953, 957, 958
See application file for complete search history.

(56) References Cited

U.S. PATENT DOCUMENTS

| | | | | |
|---|---|---|---|---|
| 6,573,089 | B1 | 6/2003 | Vann | |
| 6,620,584 | B1 | 9/2003 | Chee et al. | |
| 6,649,404 | B1 | 11/2003 | Vann et al. | |
| 6,667,159 | B1 | 12/2003 | Walt et al. | |
| 6,670,121 | B1 | 12/2003 | Hoffmann | |
| 6,812,005 | B2 | 11/2004 | Fan et al. | |
| 6,890,764 | B2 | 5/2005 | Chee et al. | |
| 6,893,824 | B2 | 5/2005 | Ito | |
| 6,905,829 | B2 | 6/2005 | Cho et al. | |
| 6,916,614 | B1 | 7/2005 | Takenaka | |
| 6,924,105 | B2 | 8/2005 | Sudo et al. | |
| 6,962,823 | B2 * | 11/2005 | Empedocles et al. | 438/3 |
| 7,123,029 | B2 | 10/2006 | Frey et al. | |
| 7,129,047 | B2 | 10/2006 | Yamashita | |
| 7,151,209 | B2 * | 12/2006 | Empedocles et al. | 438/689 |
| 2006/0160134 | A1 * | 7/2006 | Melker et al. | 435/7.1 |
| 2010/0010600 | A1 * | 1/2010 | Eriksson et al. | 607/116 |

* cited by examiner

*Primary Examiner*—Brian J Sines
(74) *Attorney, Agent, or Firm*—Albert O. Cota

(57) ABSTRACT

A biomolecule analyzing system (10) that provides an expeditious, accurate and reliable method for analyzing a biomolecule (150). The system (10) includes two substrates (12,28) each having an inner edge (14,30), an outer edge (16,32) and an inner surfaces (20,36) from where extends a multiplicity of cilia (22). To the inner edges (14,30) is attached an input tube (82) that is also attached to a biomolecule sample reservoir (90). To the outer edges (16,32) is attached an output tube (106) that is also attached to a sample deposit chamber (120). The tubes (82,106) include a plurality of conductive plates (98) that are applied an electrical charge that causes the biomolecule (150) to traverse through the tubes (82,106). When the biomolecule (150) passes through the cilia (22) signals are produced that are applied to a pair of image capturing devices (40,50). Each device (40,50) produces a signal that is applied to an electronic data processor from where a three-dimensional image of the biomolecule (150) is produced and viewed on a data monitoring device (70).

26 Claims, 4 Drawing Sheets

BIOMOLECULE ANALYZING SYSTEM

TECHNICAL FIELD

The invention generally pertains to the field of biomolecule analyzing systems, and more particularly to a biomolecule analyzing system that utilizes a pair of ciliated sensors to produce a three-dimensional image of a biomolecule under study.

BACKGROUND ART

In the fields of molecular biology, biochemistry and pharmacology an accurate and expeditious analysis of biomolecules such as recombinant deoxyribonucleic acid (DNA) is of the utmost importance: Typically, a DNA specimen is analyzed by placing the specimen into a porous gel matrix, which allows the movement of particles but impedes the rate of travel. A current is then applied to the gel matrix to produce positively and negatively charged ends of the gel matrix. Under these conditions the DNA migrates toward the positively charged end of the gel matrix. This process is used to separate DNA of different sizes and to separate newly synthesized DNA strands with labels in order to elucidate sequences of small DNA strands.

Unfortunately, the above-described process is inadequate for the sequencing of long DNA strands. DNA longer than 10 to 20 thousand bases cannot be reliably synthesized in a single polymerization reaction. To provide sequence data, the DNA synthesized in a reaction must start from the same position on the DNA strand being sequenced so that an exact base at which the reaction terminated with a label is known. If the reaction is started randomly, DNA fragments would represent all possible bases within a sample, but the DNA would be separated only by size. The result would be fragments of all possible sizes terminated with all possible bases. Even if the entire sequence of each fragment were known, the task of overlapping the fragments into a complete genome would be a difficult and error prone. Roughly forty-percent of the human genome is composed of non-functional copies of viral genes and the overlapping regions are similar throughout. The result is that some regions will be placed out of order and others will likely be omitted because they are identical to other fragments. To provide data that is based on more than the length of the DNA fragment and the terminating base of the fragment, there must be a process of controlling the orientation and the movement of the DNA to be examined.

A cyclotron is a particle accelerator device that is still used in hospitals to produce activated technetium and other isotopes that have short half lives. The device is simply a track that runs in a circular path with plates capable of carrying a charge when switches are closed. The plates are charged so that electrons are drawn one way and repelled from the opposite direction. The switches are closed at an increasing rate, which causes a particle to be repelled from one side and pulled from the other side along the track at an increasing velocity until a collision is desired. A door in the track is then opened and the accelerating electrons are ejected directly toward the substance to be bombarded with beta particles.

This principle inherent in the cyclotron could theoretically direct the movement of DNA alone, however the fragments of DNA would still be tightly condensed and no information other than the position of the DNA would be known. To remedy this problem, a linear track is placed along a linear path, and rather than charged plates, an electric field is applied such that charges of one polarity are pulled across the track, and charges having the opposite polarity are repelled. Alternatively, the field could be designed to attract a magnetic particle while repelling a charged particle. The DNA would then be pulled or pushed as an indecipherable mass. To decipher the mass, it is necessary to add another component such as an antibody. Antibodies specific to the 5' or 3' end of a DNA strand can be generated and attached to additional particles, including charged or magnetic particles.

If the 5' end of a DNA strand is attached by an antibody to a charged bead that is pulled down the linear track, and the 3' end is attached to a bead that is repelled less strongly than the 5' end is attracted, there will be a net movement along the linear track. Thus, the direction and the order of a DNA sample can be controlled. The only limitation to the length of a DNA fragment that can be moved is the length of the linear track. A linear track in conjunction with antibody bound charged beads requires a sensor that is capable of making direct observations of DNA strands.

The inventive biomolecule analyzing system that utilizes a ciliated sensor solves the problems inherent in the prior art.

A search of the prior art did not disclose any patents that read directly on the claims of the instant invention. However the following U.S. patents are considered related:

| PATENT NO. | INVENTOR | ISSUED |
|---|---|---|
| 7,129,047 | Yamashita | 31 Oct. 2006 |
| 6,924,105 | Sudo, et al | 2 Aug. 2005 |
| 6,670,131 | Hashimoto | 30 Dec. 2003 |
| 6,573,089 | Vann | 3 Jun. 2003 |

The U.S. Pat. No. 7,129,047 discloses a nucleotide detector that consists of metal particles and single-stranded thiol DNAs. The metal particles are placed on the surface of a substrate. The DNAs have sulphur atoms at their ends, which are bonded to gold particles and placed uniformly over the substrate. Therefore, once a fluorescence-labeled single-stranded DNA is hybridized with any of the thiol DNAs, a high fluorescence intensity is stably obtained. The nucleotide detector is therefore usable as a high-performance DNA sensor with a high SN ratio.

The U.S. Pat. No. 6,924,105 discloses a method for directly analyzing double-stranded DNA that is present in an analyte without degeneration. The method comprises the steps of:

(1) contacting the analyte with a double-stranded DNA recognizing substance immobilized on a support, and (2) measuring double stranded DNA that are bound to the double stranded DNA recognizing substance.

The U.S. Pat. No. 6,670,131 discloses a nucleic acid detection apparatus. The apparatus includes a nucleic acid immobilized electrode, a plurality of vessels for bringing the nucleic acid probe into contact with a subject substance, a counter electrode disposed on a bottom surface or inside surface of the vessels, and an electric circuit for applying a voltage between the nucleic acid immobilized electrode and the counter electrode. A nucleic acid is detected by inserting the nucleic acid immobilized electrode into each vessel containing the subject substance, and using the counter electrode disposed on the bottom surface or inside surface of the vessel to electrically control a reaction.

The U.S. Pat. No. 6,573,089 discloses an apparatus and method for contacting at least two chemical species: The apparatus comprises a support plate having a channel for receiving a mobile chemical species and a fiber having a second immobilized chemical specie disposed on the support plate. A portion of the fiber is exposed to the channel such that the mobile chemical species is capable of contacting the second chemical species.

For background purposes and as indicative of the art to which the invention is related reference my be made to the remaining patents located in the patent search:

| PATENT NO. | INVENTOR | ISSUED |
|---|---|---|
| 7,123,029 | Frey, et al | 17 Oct. 2006 |
| 6,916,614 | Takenaka | 12 Jul. 2005 |
| 6,905,829 | Cho, et al | 14 Jun. 2005 |
| 6,893,824 | Ito | 17 May 2005 |
| 6,890,764 | Chee, et al | 10 May 2005 |
| 6,812,005 | Fan, et al | 2 Nov. 2004 |
| 6,667,159 | Walt, et al | 23 Dec. 2003 |
| 6,649,404 | Vann, et al | 18 Nov. 2003 |
| 6,620,584 | Chee, et al | 16 Sep. 2003 |

DISCLOSURE OF THE INVENTION

The biomolecule analyzing system (BAS) disclosed herein provides a means for expeditiously, accurately and reliably producing a three-dimensional image of biomolecule under study. In its basic design, the BAS is comprised of:

A. A first substrate and a second substrate, with each substrate having an inner edge, an outer edge, an outer surface and an inner surface. From the inner surface of the first substrate extends downward a multiplicity of probes, and from the inner surface of the second substrate extends upward a multiplicity of probes, wherein the termini of the probes are spaced apart from each other and are in an anti-parallel configuration.

B. A first image capturing device that is attached to the outer surface of the first substrate, and a second image capturing device that is attached to the outer surface of the second substrate. Each of the devices is applied a signal from the respective first and second substrates, thereby causing each of the devices to produce an output.

C. An electronic data processor having a duel input that is applied from the two outputs of the first and second image capturing devices. The electronic data processor operates in combination with software to control the operation of the BAS.

D. A d-c power source having means for supplying the required electrical power levels to the BAS, wherein the outputs from the d-c power source are controlled by the electronic data processor.

E. A biomolecule passage track comprising:

(1) a non-conductive input tube having an input edge that is attached to a biomolecule sample reservoir, and an output edge that is attached to the inner edges of the first and second substrates, and (2) a non-conductive output tube having an input edge that is attached to the outer edges of the first and second substrates, and an output edge that is attached to a sample deposit chamber. The input and output tubes have means for causing a biomolecule sample applied from the biomolecule sample reservoir to sequentially traverse through the input tube, the space between the multiplicity of probes, through the output tube and terminating at the sample deposit chamber, wherein when the biomolecule passes through the area surrounding the multiplicity of spaced probes, the probes are stimulated, thereby causing a charge to be applied to the first and second substrates, from where a pair of signals are produced that are applied to the first and second image capturing devices. The pair of signals are converted to an image that is applied to and processed by the electronic data processor and viewed on a data monitoring device as a three-dimensional image.

The means for causing a biomolecule sample to sequentially traverse through the input tube, the space between the multiplicity of probes, the output tube and terminating at the sample deposit chamber is comprised of a plurality of electrically conductive plates. The plates are longitudinally spaced along the inner surfaces of the input tube, the output tube and the sample deposit chamber. The plates are electrically connected in parallel and to the d-c power source, wherein the voltage polarity and voltage magnitude applied to the plates determines the passage direction of the biomolecule and is dependent upon the polarity of the biomolecule. The voltage polarities are used by the electronic data processor to determine the biomolecule's X and Y coordinates, and the charge magnitude generated on the piezoelectric substrate is used by the electronic data processor to extrapolate the biomolecule's Z coordinate. The three X, Y and Z coordinates are used to produce the three-dimensional image that is viewed on the data monitoring device.

The probes located on the first and second substrates are preferably comprised of an array of molecular diameter cilium having a uniform length and that are located on a thin piezoelectric substrate having an irregular crystal matrix. By utilizing the piezoelectric properties of the two substrates, the ciliated substrates are forced to oscillate when an electrical charge is applied to the substrates. The applied charge is adjusted to produce the desired frequency and amplitude of oscillation required for a specific application.

The two ciliated sensor arrays are placed into an anti-parallel configuration such that each cilia termini face each other and come into the contact without resistance during a maximum oscillation. Thus, an object contacting the cilia will cause a resistance, which is the only resistance produced. Due to the irregular crystal matrix and the thin layer of the piezoelectric substrate, obstructions in the path of the cilia during maximum oscillation is observed instantaneously as a charge on the surface of the first and second substrates.

The image capturing devices, which can consist of Charge Coupled Devices (CCDs) or the like, are attached directly onto the respective piezoelectric substrates. In this configuration, maximum oscillation converts the majority of the applied charge into an expansion of the crystal matrix.

Charge maps from the cilia are transmitted directly to the electronic data processor as either a series of still images or as video. The charge maps inherently contain a Cartesian X-Y coordinate plane, but each charge recorded on that plane also has an associated charge magnitude. The magnitude of the charge corresponds to the degree of interference in the path of the cilia during maximum oscillation. As such, the magnitude can be extrapolated by the electronic data processor into a Z coordinate that is integrated into the Cartesian coordinate plane to produce three dimensional images of an object located between the ciliated sensor arrays.

In order to optimize information gathered from the ciliated sensors, it is necessary to control the location and movement of the biomolecules passing through the sensor space. While it is difficult to control the simultaneous position, motion and orientation of a biomolecule, it is possible to control the position and motion of biomolecules after they have been attached to other biomolecules. This allows the BAS to control the position, motion, and orientation of a biomolecule under study by separately controlling the position of two attached biomolecules. This requires a process of movement control and a process of attachment to the biomolecule under study. The two molecules are attached by means of antibodies, while charged beads provide motion control. In all cases, the antibodies and the charged beads are combined to form a single species before they are processed by the BAS.

Most linear form biomolecules have differentiated terminal ends. Whether this is N-terminus/C-terminus or 3'/5' does not matter. Specific antibodies are cultured for each set of terminal ends. Antibodies specific to one end are bound to a charged particle and antibodies specific to the opposite end are bound to particles of the opposite charge. The reaction that follows incubates the biomolecule in the presence of the charged bead-linked antibodies. After the reaction, a sample biomolecule is placed onto the biomolecule passage track.

The input and output tubes that comprise the biomolecule traversing track can consist of any non-reactive DNAse/RNAse free material such as polyethylene, quartz, glass, etc. The overall length of the tubes must be at least as long as the biomolecule under study on each side of the sensor in order to keep the entire biomolecule inside the charged track. For human chromosomes there would need to be at least 12 centimeters of track on each side of the cilliated sensor.

Each tube includes a plurality of conductive plates that are applied a charge that can vary between positive and negative charges as required and have an applied charge adjusted to control the power exerted on each of the charged ends of a sample biomolecule. This allows the sample to be simultaneously pulled forward as well as exert a resistance on the opposite end in order to pull the sample biomolecule taught, thereby making all monomers equally available to the cilia of the ciliated sensor array. The inside of the track is as wide as the sensor array, but only as high as needed for the passage of the charge bead and a single biomolecule. The charged beads force all biomolecules an equal distance apart as they move through the biomolecule traversing track. The track must be longer than the biomolecule on both sides in order to maintain tension in the linear biomolecule.

Due to the rapid rate of sensor oscillation and the controlled rate of biomolecule movement through the sensor space, hundreds to thousands of images can be recorded for each biomolecule as it passes through the sensor array. For polymers comprised of long chains of identifiable monomers, this allows overlapping segments to be integrated as the polymer passes, so that a specific order of monomers within the polymer can be elucidated instantly. Given the rate of polymer integration and the control of biomolecule movement, error correction can be built into the BAS. When resolution of a monomer or region of the polymer is poor, the charge on the track plates can reverse movement of the biomolecule in order to reread sections of the polymer as necessary to output a complete order of monomeric construction. In this manner, the order of monomers in a polymer several billion monomers in length can be elucidated in under an hour.

A folded biomolecule, which is a biomolecule that folds into a specific structure that allows the biomolecule to perform a specific role, can have a single charged bead antibody targeted at any surface on the biomolecule. The charged track is then used to force the biomolecule into the sensor space. Images of the biomolecule are then recorded or integrated into video models of the biomolecule's action. For the purpose of video models, the frequency of sensor oscillation can be increased to improve the image resolution.

In the event that known monomers within a biomolecule of interest are too small to be resolved with current molecular diameter fibers, it is possible to enhance resolution with the binding of additional markers. Antibodies are cultured for specificity to each known monomer. Each unique antibody is bound to an uncharged bead of unique size which can be easily resolved. Long linking biomolecules are used to prevent crowding of the beads around a biomolecule backbone. A backbone is defined as any biomolecule having a linkage between monomers that form a straight line. The cultured antibodies are added at the same time as the terminal end of the backbone charged bead antibodies. When the biomolecule passes through the sensor space the beads will be spaced apart in a spiral around the biomolecule backbone by stearic hindrance, and the unique size of each bead can easily be read as one of the known monomers in the biomolecule being studied. Because the beads are spaced such that they are in direct contact, any empty space is interpreted as a missing monomer. An empty space, which differs from a false signal, can occur when an antibody bead that is being used as a marker fails to bind.

The cilia is minimally conductive and highly stable. As material science improves it would be ideal to construct cilia of a one molecule diameter. However, for the implementation of the BAS, single-walled carbon nanotubes having a diameter ranging from of 0.3 to 30.0 nanometers will suffice. The nanotubes are grown within a chemical vapor deposition chamber using an applied electrical field to force a uniform direction of growth. Spots of a metal catalyst approximately three angstroms in diameter and approximately one angstrom apart are utilized to determine the diameter of the nanotubes. The nanotubes can also be grown directly on the crystal substrate or on a thin layer polymer.

If the nanotubes are grown on a thin layer polymer such as vinyl or nitrocellulose, the polymer can later be fixed to an appropriate crystal substrate by applying beat. The polymer should have a thickness as thin as possible in order to conduct pressure from the cilia to the crystal beneath the polymer. Normally, when a charge is generated on a crystal surface by applying pressure on the crystal, the charge is distributed across the surface. This results in a complete loss of charge localization and mapping. To avoid this problem, Gallium nitrate (GaN) or nanocrystal can be used for the crystal matrix. GaN, while continuous in structure, has such an irregular crystal matrix that a charge or density changes are localized and transient. Nanocrystals that are mechanically confined have separate crystals each having a unique surface charge in response to stimulation such as that of the cilia. The crystal matrix, whether it is GaN or nanocrystal, must also be thin so that pressure will result in a charge on the opposite surface of the crystal layer.

The piezoelectric effect inherent in the crystal substrate itself, or a second crystal, can be stimulated by a charge to generate an oscillation in each of the anti-parallel sensors. By modifying the amplitude of the charge applied to the crystal, a minimum and maximum oscillation will control the size of the sensor space and frequency at which the cilia contact the biomolecules in the sensor space. This can be used to increase or decrease the frequency of observations recorded.

With XYZ mapping, a three-dimensional image is constructed for any biomolecule that passes through the sensor array. Under analysis these images can be compared to any standard that has been previously analyzed and unique molecules or monomers within a polymer can be identified. In the case of polymers, adequately directing the movement of the polymer through the sensor space allows for absolute observation of the order in which monomer units occur within the polymer being analyzed.

These and other objects and advantages of the present invention will become apparent from the subsequent detailed description of the preferred embodiment and the appended claims taken in conjunction with the accompanying drawings.

BEST MODE FOR CARRYING OUT THE INVENTION

Figure 1:
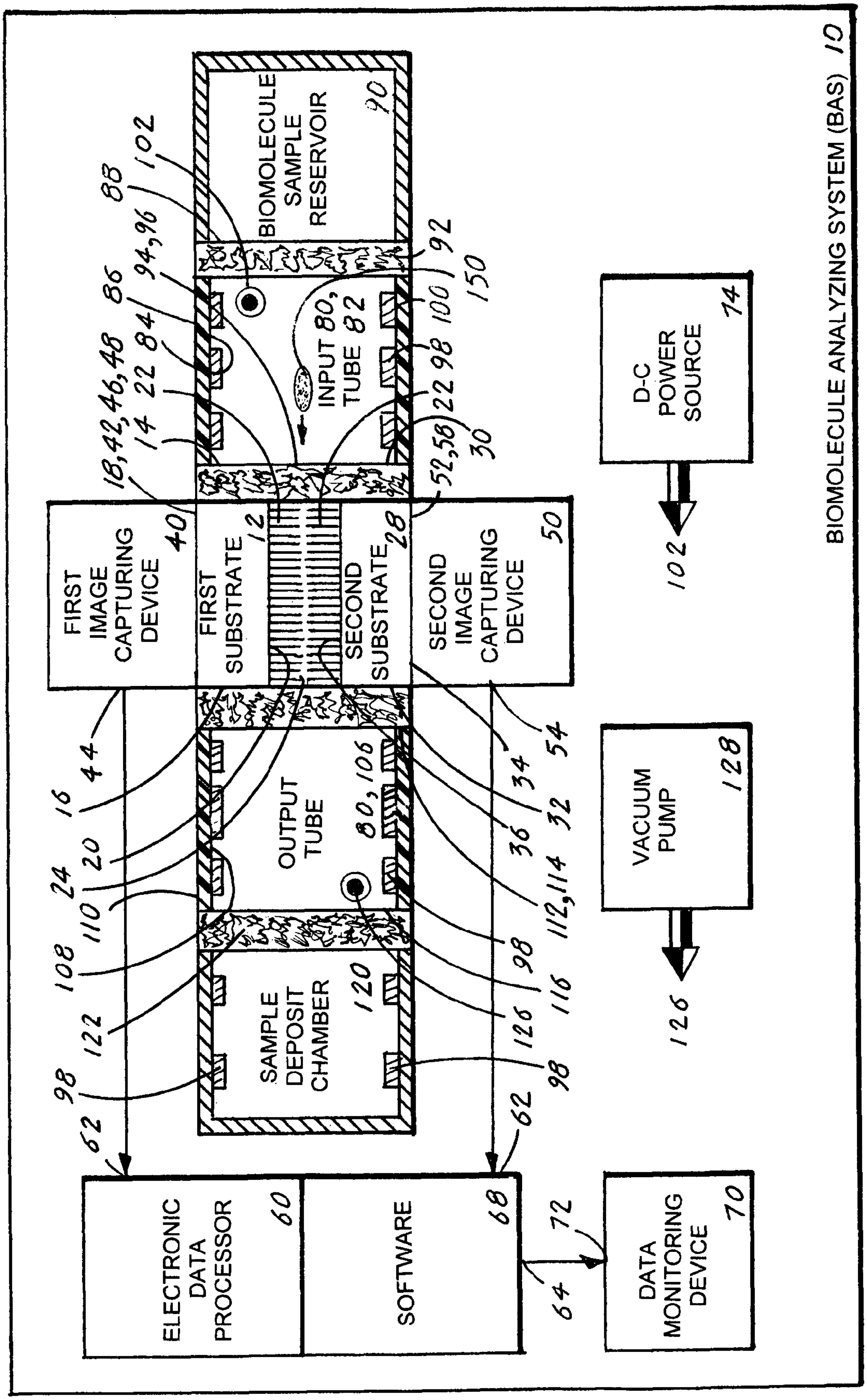
FIG. 1 is a block diagram of the overall biomolecule analyzing system.

The best mode for carrying out the invention is presented in terms of a preferred embodiment for a biomolecule analyzing system 10 (hereinafter "BAS 10"). The BAS 10, as shown in FIGS. 1-4, is comprised of the following major elements: a first substrate 12, a second substrate 28, a first image capturing device 40, a second image capturing device 50, an electronic data processor 60, software 68, a data monitoring device 70, a d-c power source 74 and a biomolecule traversing track 80.

The first substrate, as shown in FIG. 1, includes an inner edge 14, an outer edge 16, an outer surface 18, and an inner surface 20. From the inner surface 20 extends downward a multiplicity of cilia 22, with each cilium 22 having a uniform length and terminus 24.

The second substrate 28, as shown in FIG. 1, includes an inner edge 30, an outer edge 32, an outer surface 34 and an inner surface 36. From the inner surface 36 extends upward a multiplicity of cilia 22, with each cilium 22 also having a uniform length and a terminus 24. The two termini 24 of the cilia 22 are spaced apart from each other in an anti-parallel configuration, that is, the termini 24 extending downward from the first substrate 12 face the termini 24 extending upward from the second substrate 28. The space between the two termini 24, which do not have to be in alignment, ranges from 2.0 nanometers to 6.0 nanometers which suffices for most DNA applications. Larger molecules such as protein strands may require a space of as much as 20.0 nanometers.

The first and second substrates 12,28 are comprised of a thin piezoelectric material having an irregular crystal matrix. The preferred material for the first and second substrates is GaN. However, the substrate can also be made of a nanocrystal layer that is typically comprised of 0.5 nanometer crystals that are trapped in close proximity to fill the space of the two substrates 12,28.

Each of the multiplicity of cilia 22 that extend from the inner surfaces 20,36 of the first and second substrates 12,28 is preferably comprised of a single-walled nanotube each having an inner tip (terminus) and an outer tip. The nanotube has a diameter ranging from 0.3 to 30.0 nanometers and a length ranging from 6.0 to 45.0 nanometers. The nanotubes are preferably grown directly on the crystal substrate. However, the nanotubes can also be grown on a thin cross-linked layer polymer selected from the group consisting of nitocellulose or vinyl. The polymer can be later attached to a substrate having an irregular crystal matrix by applying heat. Additionally, the nanotubes can be produced by a process wherein:

a) a ferrous material is attached to the inner tip of each the nanotube, b) an adhesive layer is applied to the inner surfaces of the first and second substrates 12,28, c) a magnetic force is releasably applied to the outer surfaces of the first and second substrates 12,28 wherein the magnetic force pulls the ferrous tip of the nanotubes into the adhesive layer or adhesive film, resulting in a space filling placement of the nanotubes in a uniform direction, and d) the outer tip of each the nanotube is trimmed to a length ranging from 6.0 to 45.0 nanometers.

By utilizing the piezoelectric properties of the substrates 12,28, the cilia 22 is forced to oscillate when an electrical charge is applied the substrates 12,28. The applied charge can be adjusted to produce the desired frequently and amplitude of the oscillation required for a specific application. Any object that contacts or obstructs the cilium 22 will cause a resistance to be produced that in turn causes an oscillation. Due to the irregular crystal matrix of the substrates 12,28 the oscillation produced can be observed instantaneously as a charge on the outer surface 18,34 of the first and second substrates 12,28 respectively. The charge from the first and second substrates 12,28 is applied respectively to the first and second image capturing devices 40,50. The first and second image capturing devices 40,50 can be selected from the group consisting of a charge-coupled device (CCD), a metal oxide semiconductor (MOS), or a charge bubble device.

The first image capturing device 40 is attached to the outer surface 18 of the first substrate 12 by a first substrate attachment means 48 that preferably is comprised of an adhesive. The first device 40 has an input 42 and a first output 44. The input 42 is applied the charge 46 from the first substrate 12 and the first output 44 is applied to the electronic data processor 60 as described infra.

The second image capturing device 50 is attached to the outer surface 34 of the second substrate 28 by a second substrate attachment means 58 that preferably is also comprised of an adhesive. The second device 50 has an input 52 and a second output 54. The input 52 is applied the charge 46 from the second substrate 28 and the second output is applied to the electronic data processor 60 as described infra.

The first and second outputs 44,54 from the first and second image capturing devices 40,50 contain X and Y coordinates of the applied charge 46 as well as the magnitude of the charge 46. The magnitude of the charge is extrapolated by the electronic data processor 60 into a Z coordinate to complete an X, Y and Z coordinate map that is subsequently viewed as a three-dimensional image on the data monitoring device 70.

As shown in FIG. 1, the first output 44 and the second output 54 from the first and second image capturing devices 40,50 are applied as a dual input 62 to the electronic data processor 60. The processor 60 can be selected from a group consisting of a personal computer (PC), a microcontroller or a microprocessor. Whichever processor is selected, it is operated by means of a BAS software 68 that in combination with the processor 60 controls the operation of the BAS 10.

Figure 2:
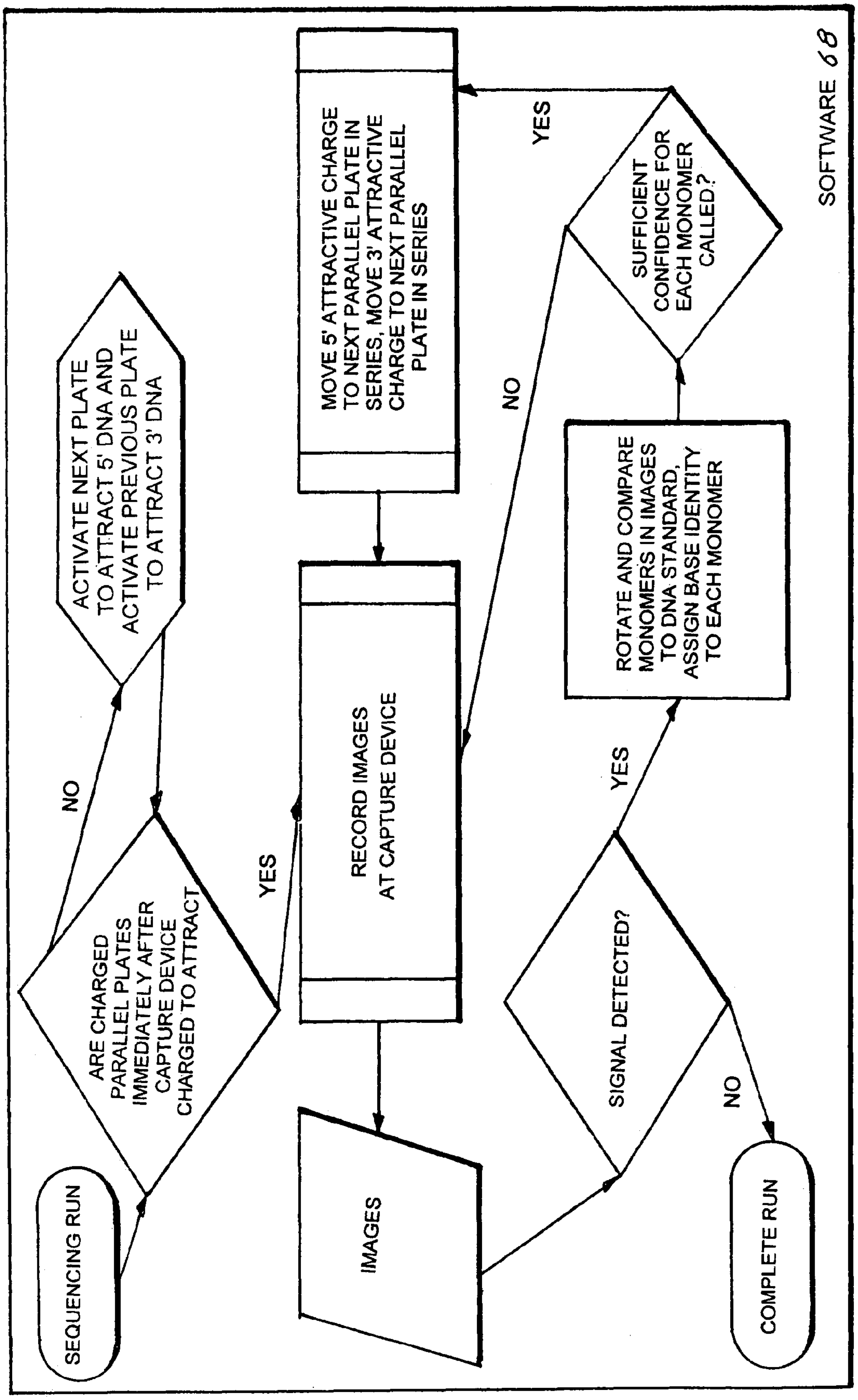
FIG. 2 is a block diagram of the BAS software.
Figure 3:
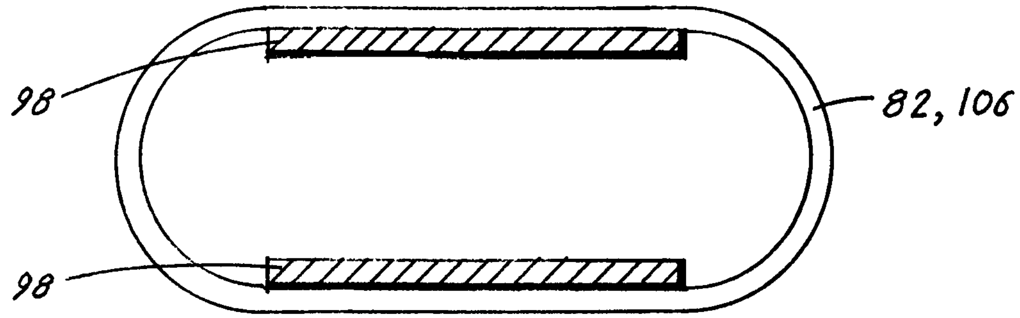
FIG. 3 is an elevational end view of an input tube or an output tube having attached to their upper and lower inner surfaces an upper conductive plate and a lower conductive plate respectively.

The BAS software 68, as shown in FIG. 2, is comprised of the following steps:

a) commence sequence run, b) charge the conductive plates 98 located in the input tube 82 to allow the biomolecule 150 in the biomolecule sample reservoir 90 to traverse into the space located between the cilia 22, c) charge the first and second substrates 12,28 to allow the first and second image capturing devices 40,50 to record images, d) integrate the images from the first and second image capturing devices 40,50 and rotate the images on all axes and compare the images to preset monomers until a match is identified, e) save the image and sequence data to a file in the electronic data processor, f) repeat steps b) through e) if matches for each monomer in the image can not be determined within a preset confidence level, g) stop the voltage applied to the first and second substrates 12,28, h) alter the charge on the conductive plates 98 located in the input tube 82 and in the output tube 106 so that the biomolecule 150 is drawn forward into the input tube 82 by an increment assigned before beginning the sequence run, i) charge the first and second substrates 12,28 and allow the image capture devices 40,50 to record the images, j) stop the voltage applied to the first and second substrates 12,28 if the recorded image contains no detectable monomers, and alter the charge applied to the plates 98 located on the input and the output tubes 82,106 to allow the biomolecule 150 to be pushed completely into the sample deposit chamber 120, k) if monomers are detected, the images from the image capturing devices 40,50 are integrated and then the integrated monomer images are rotated on all axes and compared to preset monomers until a match is identified, l) save the image and sequence data to a file in the electronic data processor, and m) repeat steps f) through l) until no monomers are detected at step j).

The electronic data processor 60, as shown in FIG. 1, has an output 64 that is applied to the input 72 of the data monitoring device 70. The device 70 has the capability of producing three-dimensional images that can be directly viewed or produced as hard copies.

The electrical power to operate the BAS is provided by a reversible d-c power source 74, as shown in FIG. 1, that can consist of an electronic regulated power supply or a set of rechargeable batteries. In either case, the output 76 of the reversible d-c power source 74 is controlled by the electronic data processor 60 and is applied to the BAS 10 via a cable (not shown) that is connected to an electrical input connector 102. The input connector 102 can be located at any location on the BAS 10 that allows the power to be conveniently directed to the BAS elements requiring electrical power.

The final element that comprises the major elements of the BAS 10 is the biomolecule passage track 80. The track 80 is comprised of a sterile input tube 82 and a sterile output tube 106, as shown in FIG. 1. Both tubes are formed of a non-reactive DNAse/RNAse enzyme free material that can be selected from the group consisting of polyethylene, quartz or glass. The internal space of the tubes 82,106 must be at least as wide as the first and second substrates 12,28 and have a height ranging from 2.0 to 10.0 nanometers which is sufficient for most DNA applications.

The input tube 80 is comprised of an inner surface 84, an outer surface 86, an input edge 88, an output edge 94 and a plurality of electronically conductive plates 98.

The input edge 88 is dimensioned to be hermetically attached to a removable biomolecule sample reservoir 90 by a reservoir attachment means 92 that is selected from the group consisting of an adhesive, ultrasonic bonding or a heat fusion process. The output edge 94 is dimensioned to be hermetically attached by an input tube/substrate attachment means 96 to at least the inner edges 14,30 of the first and second substrates 12,28. The input tube/substrate attachment means can also be selected from the group consisting of an adhesive, ultrasonic bonding or a heat fusion process.

The biomolecule sample reservoir 90 is designed and dimensioned to accept a sample biomolecule 150 that has been prepared for analyses. The preparation of the sample biomolecule 150 can be accomplished by taking the following steps:

a) place a free biomolecule 150 in a solution, b) add charged bead-antibodies to a first end of the biomolecule and charged bead-antibodies having an opposite polarity to a second end of the biomolecule, c) add additional antibodies or labels to a biomolecule 150 as required, for a specific purpose, d) incubate the biomolecule with the antibodies to allow the antibodies to locate a target and to bind to the target, e) transfer the mixture obtained from steps a) through d) into said biomolecule sample reservoir 90, f) thicken the biomolecule mixture, if necessary, g) attach said biomolecule sample reservoir to the input edge 88 of said input tube 82, and, h) commence a sample run.

The input tube 82 is dimensioned to include a plurality of electrically conductive plates 98 that are longitudinally spaced along the inner surface 84 of the tube 82, as shown in FIGS. 1, 3, 4, and 5. The plates 98 are attached to the inner surface 84 by a plate attachment means 100 that is preferably comprised of an adhesive.

Figure 6:
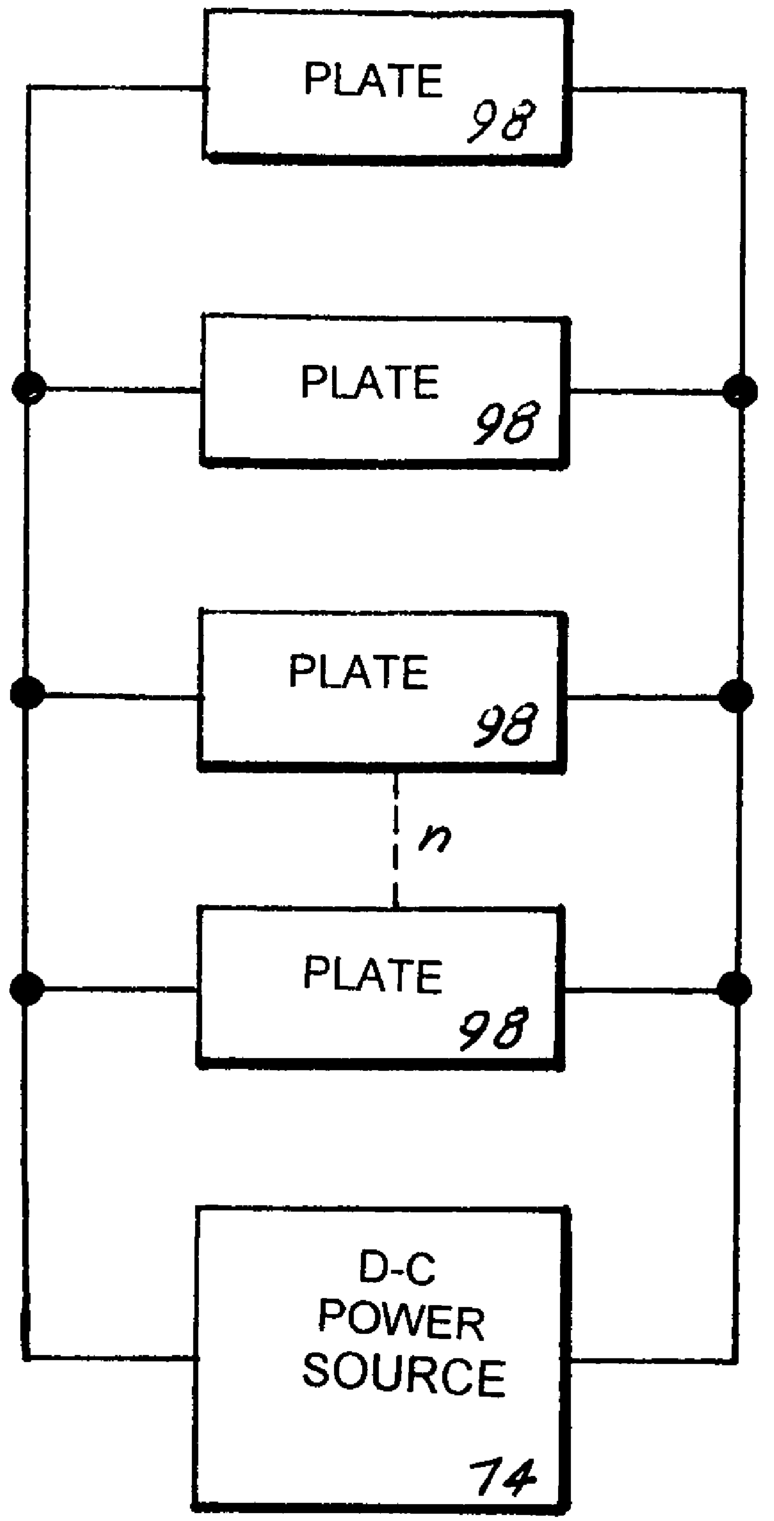
FIG. 6 is a block diagram showing the plurality of electrically conductive plates connected in parallel to a d-c power source.

The electrical plates 98 are electrically connected in parallel, as shown in FIG. 6, to the reversible d-c power source 74 via the hermetic electrical input connector 102. The polarity and the magnitude of the charge 46 that is applied to the plates 98 is dependent upon the polarity of the biomolecule sample 150 that is under study. The voltage polarities and the charge magnitude allow the biomolecule to hover within the inner surface of the input tube 82. The polarities also determine the direction in which the biomolecule 150 will traverse through the tube 82, and the biomolecule's X and Y coordinates. The biomolecule's Z coordinate is extrapolated by the electronic data processor 60. The X, Y and Z coordinates ultimately are used to produce the three-dimensioned image that is viewed on the data monitoring device 70.

When a biomolecule 150 traverses through the input tube and through the space between the cilium 22 on the first and second substrates 12,28, the cilium 22 is stimulated which produces the charge that is applied to the first and second substrates 12,28. The substrate charge is then applied to the first and second image capturing devices 40,50, where the charge is converted into an image that is applied to and processed by the electronic data processor 60 and viewed on the data monitoring device 70 as the three-dimensional image.

The output tube 106 is comprised of an inner surface 108, an outer surface 110, an inner edge 112, an output edge 116 and a plurality of electrically conductive plates 98.

The input edge 112 is dimensioned to the hermetically attached by a substrate attachment means 114, which preferably consists of an adhesive, to at least the outer edges 16,32 of the first and second substrate 12,28. The output edge 116 is dimensioned to be hermetically attached to the removable sample deposit chamber 120 by a chamber attachment means 122 that is selected from the group consisting of an adhesive, ultrasonic bonding or a heat fusion method.

The output tube 106 is dimensioned to also include a plurality of electrically conductive plates 98 that are longitudinally spaced along the inner surface 108 of the output tube 106, as shown in FIGS. 1 and 2. The plates 98, which consist of a metal selected from the group consisting of gold, silver or copper, are attached to the inner surface 108 by a plate attachment means 100 that preferably consists of an adhesive.

The plates 98 attached to the output tube 106 are also electrically connected in parallel and to the reversible d-c power source 74 via the hermetic electrical input connector 102. The polarity and the magnitude of the voltage applied to the plates 98 causes the biomolecule sample 150 under study to hover within the inner surface 84 of the output tube 106 and to continue traversing through the output tube 106 and into the sample deposit chamber 120, from where the biomolecule 150 can be discarded or reused. The sample deposit chamber 120 must also include to least one conductive plate 98 to finally attract the biomolecule 150 into the chamber 120.

Figure 4:
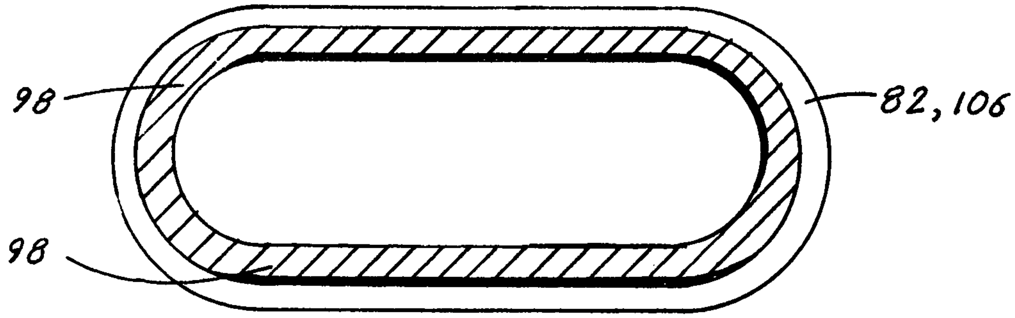
FIG. 4 is an elevational end view of an input tube or an output tube having attached a circumferential conductive plate.
Figure 5:
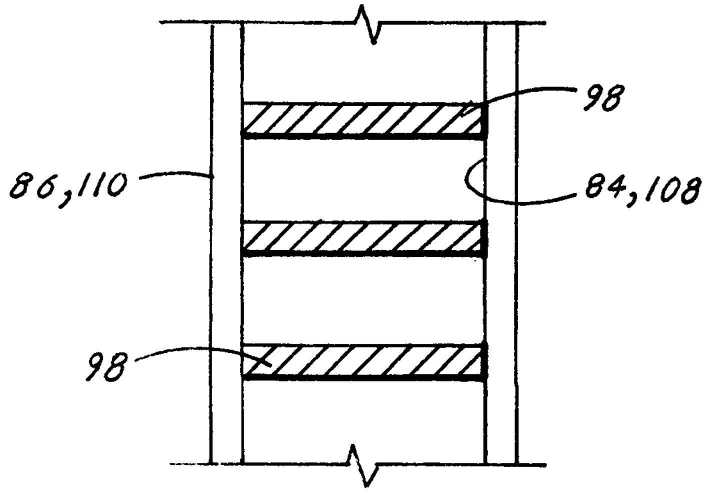
FIG. 5 is a partial top plan view of an input tube or an output tube showing a plurality of spaced conductive plates.

The plurality of longitudinally spaced conductive plates 98 can be comprised of two design configurations. In the first design, the plates 98 are each comprised of an upper conductive plate 98 and a lower conductive plate 98, a shown in FIG. 3. In the second design each conductive plate 98 is comprised of a circumferential conductive plate 98, as shown in FIG. 4. FIG. 5 has a partial top plan view of an input tube 82 or an output tube 106 showing a plurality of spaced conductive plates 98.

To further enhance the utility of the BAS 10, a hermetic vacuum input port 126, that can extend from a surface of the input tube 82 or the output tube 106, is included in the BAS 10. To the vacuum input port 126 is attached a vacuum pump 128 that creates a partial vacuum within the input tube 82, the output tube 106 and the space between the anti-parallel cilium 22. The partial vacuum reduces background noise and increases the resolution of the three-dimensional image.

While the invention has been described in detail and pictorially shown in the accompanying drawings it is not to be limited to such details, since many changes and modifications may be made to the invention without departing from the spirit and the scope thereof. For example, other structures and methods can be utilized to cause a biomolecule 150 to traverse through a pair of hermetically sealed tubes 82,106. Hence, it is described to cover any and all modifications and forms which may come within the language and scope of the claims.

BIOMOLECULE ANALYZING SYSTEM (BAS)
Element Designation
(For convenience of said Examiner, not part of said specification)

| | |
|---|---|
| 10 | Biomolecule Analyzing System (BAS) |
| 12 | First Substrate |
| 14 | Inner Edge |
| 16 | Outer Edge |
| 18 | Outer Surface |
| 20 | Inner Surface |
| 22 | Cilia |
| 24 | Terminus |
| 26 | |
| 28 | Second Substrate |
| 30 | Inner Edge |
| 32 | Outer Edge |
| 34 | Outer Surface |
| 36 | Inner Surface |
| 38 | |
| 40 | First Image Capturing Device |
| 42 | Input |
| 44 | First Output |
| 46 | Charge |
| 48 | First Substrate Attachment Means |
| 50 | Second Image Capturing Device |

-continued

BIOMOLECULE ANALYZING SYSTEM (BAS)
Element Designation
(For convenience of said Examiner, not part of said specification)

| | |
|---|---|
| 52 | Input |
| 54 | Second Output |
| 56 | Charge |
| 58 | Second Substrate Attachment Means |
| 60 | Electronic Data Processor |
| 62 | Duel Input |
| 64 | Output |
| 66 | |
| 68 | Software |
| 70 | Data Monitoring Device |
| 72 | Input |
| 74 | DC Power Source |
| 76 | Outputs |
| 78 | |
| 80 | Biomolecule Traversing Track |
| 82 | Input Tube |
| 84 | Inner Surface |
| 86 | Outer Surface |
| 88 | Input Edge |
| 90 | Biomolecule Sample Reservoir |
| 92 | Reservoir Attachment Means |
| 94 | Output Edge |
| 96 | Substrate Attachment Means |
| 98 | Conductive Plate |
| 100 | Plate Attachment Means |
| 102 | Electrical Input Connector |
| 104 | |
| 106 | Output Tube |
| 108 | Inner Surface |
| 110 | Outer Surface |
| 112 | Input Edge |
| 114 | Substrate Attachment Means |
| 116 | Output Edge |
| 118 | |
| 120 | Sample Deposit Chamber |
| 122 | Chamber Attachment Means |
| 124 | |
| 126 | Vacuum Input Port |
| 128 | Vacuum Pump (optional) |
| 130 | |
| 150 | Biomolecule |

The invention claimed is:

1. A biomolecule analyzing system (BAS) comprising:

a) a first substrate and a second substrate, wherein each substrate comprises a piezoelectric material having an irregular crystal matrix, said substrates also having an inner edge, an outer edge, an outer surface and an inner surface, wherefrom the inner surface of said first substrate extends downward a multiplicity of probes, and from said inner surface of said second substrate extends upward a multiplicity of probes, wherein said probes include cilia comprising single-walled carbon nanotubes, wherein the termini of said probes are spaced apart from each other and are in an anti-parallel configuration, b) a first image capturing device that is attached to said outer surface of said first substrate, and a second image capturing device that is attached to said outer surface of said second substrate, wherein each said device is applied a signal from said respective first and second substrates, thereby causing each of said devices to produce an output, c) an electronic data processor having a duel input that is applied from said two outputs of said first and second image capturing devices, wherein said processor operates in combination with software to control the operation of said BAS, d) a d-c power source having means for supplying the required electrical power levels to said BAS, wherein the outputs from said d-c power source are controlled by said electronic data processor, e) a biomolecule passage track comprising:

(1) a non-conductive input tube having an input edge that is attached to a biomolecule sample reservoir, and an output edge that is attached to the inner edges of said first and second substrates, and (2) a non-conductive output tube having an input edge that is attached to the outer edges of said first and second substrates, and an output edge that is attached to a sample deposit chamber, wherein said input and output tubes having means for causing a biomolecule sample applied from said biomolecule sample reservoir to sequentially traverse through said input tube, the space between said multiplicity of probes, through said output tube and terminating at said sample deposit chamber, wherein when the biomolecule passes through the area surrounding said multiplicity of spaced probes, said probes are stimulated, thereby causing a charge to be applied to said first and second substrates, from where a pair of signals are then produced that are applied to said first and second image capturing devices where the input signals are converted to an image that is applied to and processed by said electronic data processor and viewed on a data monitoring device as a three dimensional image.

2. The BAS as specified in claim 1 wherein the material for said first and second substrates is selected from the group consisting of GaN, galium compounds and mechanically confined nanocrystals.

3. The BAS as specified in claim 2 wherein said nanotubes each having:

a) an inner tip and an outer tip, b) a ferrous material that is attached to the inner tip of each said nanotubes, c) an adhesive layer applied to the inner surfaces of said first and second substrates, d) a magnetic force releasably applied to the outer surface of said first and second substrates, wherein the magnetic force pulls the ferrous tip of the nanotubes into the adhesive layer resulting in a space filling placement of said nanotubes with a uniform direction, and e) trim the outer tip of each said nanotube to a length ranging from 6.0 to 45.0 nanometers.

4. The BAS as specified in claim 1 wherein said first and second image capturing devices are selected from the group comprising of a CCD, a MOS and a charge bubble device.

5. The BAS as specified in claim 1 wherein said d-c power source is comprised of a utility-powered regulated d-c power supply.

6. The BAS as specified in claim 1 wherein said means for causing a biomolecule sample to sequentially traverse through said input tube, the space between said multiplicity of probes, said output tube and terminating at said sample deposit chamber is comprised of a plurality of electrically conductive plates that are longitudinally spaced along the inner surfaces of said input tube, said output tube and said sample deposit chamber, wherein said plates are electrically connected in parallel and to said d-c power source, wherein said voltage polarity and voltage magnitude applied to said plates determines the passage direction of the biomolecule and is dependent upon the polarity of the biomolecule, wherein the voltage polarities are used by said electronic data processor to determine said biomolecule's X and Y coordinates and the voltage magnitude is used by said electronic data processor to extrapolate said biomolecule's Z coordinate, wherein the three coordinates are used to produce the three-dimensional image that is viewed on said data monitoring device.

7. A biomolecule analyzing system (BAS) comprising:

A. a first substrate comprising a piezoelectric material having an irregular crystal matrix, said first substrate also having an inner edge, an outer edge, an outer surface and an inner surface, wherefrom said inner surface extends downward a multiplicity of cilia, with each cilium comprising a single-walled carbon nanotube having a terminus, B. a second substrate comprising a piezoelectric material having an irregular crystal matrix, said second substrate also having an inner edge, an outer edge, an outer surface and an inner surface, wherefrom said inner surface extends upward a multiplicity of cilia, with each cilium comprising a single-walled carbon nanotube having a terminus, wherein the two termini of said cilium are spaced apart from each other in an anti-parallel configuration, C. a first image capturing device that is attached to the outer surface of said first substrate by a first substrate attachment means , said first device having an input and a first output, wherein the input is applied a signal from said first substrate, D. a second image capturing device that is attached to the outer surface of said second substrate by a second substrate attachment means, said second device having an input and a second output, wherein the input is applied a signal from said second substrate, E. an electronic data processor having a duel input and an output, wherein the inputs are respectively applied the first output and the second output from said first and second image capturing devices, F. a BAS software program that operates in combination with said electronic data processor to control the operation of said BAS, G. a data monitoring device having an input that is connected to the output of and controlled by said electronic data processor, H. a reversible d-c power source that supplies the required electrical power levels to operate said BAS, wherein the outputs of said d-c power source are controlled by said electronic data processor, I. a biomolecule passage track comprising:

a) a sterile input tube having:

(1) an inner surface, (2) an outer surface, (3) an input edge that is dimensioned to be hermetically attached to a removable biomolecule sample reservoir by a reservoir attachment means, wherein said reservoir is dimensioned to accept a biomolecule that has been prepared for analyses, (4) an output edge that is dimensioned to be hermetically attached by an input/substrate attachment means to at least the inner edges of said first and second substrates, (5) a plurality of electrically conductive plates that are longitudinally spaced along the inner surface of said input tube and that are attached thereto by a plate attachment means, wherein said plates are electrically connected in parallel and to said reversible d-c power source via a hermetic electrical input connector that can extend through a surface of said input tube, wherein the polarity of the voltage charge that is applied to said plates is dependent upon the polarity of a biomolecule sample under study, wherein the polarity of the voltage charge determines the biomolecule's X and Y coordinates and the magnitude of the voltage charge is utilized by said electronic data processor to extrapolate the biomolecule's Z coordinate, wherein when a biomolecule traverses from said biomolecule sample reservoir, through said input tube and through the space between said cilium on said first and second substrates, said cilium is stimulated which produces the charge on said first and second substrates, wherein the charge is then applied to said first and second image capturing devices where the charge is converted into an image that is applied to and processed by said electronic data processor and viewed on said data monitoring device as a three-dimensional image, b) a sterile output tube having:
 (1) an inner surface,
 (2) an outer surface,
 (3) an input edge that is dimensioned to be hermetically attached by a substrate attachment means to at least the outer edges of said first and second substrates,
 (4) an output edge that is dimensioned to be hermetically attached to a removable sample deposit chamber by a chamber attachment means,
 (5) a plurality of conductive plates that are longitudinally spaced along the inner surface of said output tube and that are attached thereto by a plate attachment means, wherein said plates are electrically connected in parallel and to the reversible d-c power source via a hermetic electrical input connector that can extend from a surface of said input tube or said output tube, wherein the polarity and the magnitude of the voltage applied to said plates causes the biomolecule sample under study to continue traversing through said output tube and into said sample deposit chamber, from where the biomolecule can be discarded or reused.

8. The BAS as specified in claim 7 wherein said cilia is forced to oscillate when an electrical charge is applied across said first and second substrates.

9. The BAS as specified in claim 8 wherein the material of said first and second substrates is comprised of GaN or a nanocrystal layer.

10. The BAS as specified in claim 8 wherein said cilia is comprised of single-walled carbon nanotubes having a diameter ranging from 0.3 to 30.0 nanometers and a length ranging from 6.0 to 45.0 nanometers.

11. The BAS as specified in claim 10 wherein said cilium are grown directly on a crystal substrate or on a thin cross-linked layer polymer consisting of nitro cellulose or vinyl.

12. The BAS as specified in claim 7 wherein the space between said cilia when said cilia is at rest, ranges from 2.0 to 10.0 nanometers.

13. The BAS as specified in claim 7 wherein said image capturing device is selected from the group consisting of a CCD, a MOS and a charge bubble device.

14. The BAS as specified in claim 7 wherein said cilia substantially fills the area encompassing the inner surface of said first and second substrates.

15. The BAS as specified in claim 7 wherein said first output and said second output from said first and second image capturing devices contain the X and Y coordinates of the applied voltage charge and the magnitude of the charge, wherein the magnitude of the charge is extrapolated by said electronic data processor to produce a Z coordinate to complete an X, Y and Z coordinate map, which is subsequently converted by said electronic data processor into a three-dimensional image that is viewed on said data monitoring device.

16. The BAS as specified in claim 7 wherein said BAS software is comprised of the following steps:

a) commence sequence run,
b) charge said conductive plates located in said input tube to allow the biomolecule in said biomolecule sample reservoir to traverse into the space located between said cilia,
c) charge said first and second substrates to allow said first and second image capturing devices to record images,
d) integrate the images from said first and second image capturing devices and rotate the images on all axes and compare the images to preset monomers until a match is identified
e) save the image and sequence data to a file in the said electronic data processor,
f) repeat steps b) through e) if matches for each monomer in the image can not be determined within a preset confidence level,
g) stop the voltage applied to said first and second substrates,
h) alter the charge on said conductive plates located in said input tube and in said output tube so that the biomolecule is drawn forward into said input tube by an increment assigned before beginning the sequence run,
i) charge said first and second substrates and allow said image capture devices to record the images,
j) stop the voltage applied to said first and second substrates if the recorded image contains no detectable monomers, and alter the charge applied to said conductive plates located on said input and the output tubes to allow the biomolecule to be pushed completely into said sample deposit chamber,
k) if monomers are detected, the images from said image capturing devices are integrated and then the integrated monomer images are rotated on all axes and compared to preset monomers until a match is identified,
l) save the image and sequence data to a file in said electronic data processor, and
m) repeat steps f) through l) until no monomers are detected at step j).

17. The BAS as specified in claim 7 wherein the internal space of said input tube and said output tube is at least as wide as said first and second substrates and have a height ranging from 2.0 to 50.0 nanometers.

18. The BAS as specified in claim 7 wherein said input tube/substrate attachment means, said biomolecule reservoir attachment means and said sample deposit attachment means is selected from said group consisting of an adhesive, ultrasonic bonding and a heat fusion process.

19. The BAS as specified in claim 7 wherein said first substrate attachment means, said second substrate attachment means and said plate attachment means comprises an adhesive.

20. The BAS as specified in claim 7 wherein said sample deposit chamber further comprises at least one electrically conductive plate that finally attracts the biomolecule under study into said chamber.

21. The BAS as specified in claim 7 wherein said plurality of longitudinally spaced conductive plates are each comprised of an upper conductive plate and a lower conductive plate.

22. The BAS as specified in claim 7 wherein said plurality of longitudinally spaced conductive plates are each comprised of a circumferential conductive plate.

23. The BAS as specified in claim 7 further comprising a charged bead-antibody that is permanently attached to the biomolecule, wherein the antibody causes the biomolecule to traverse through said input tube and said output tube in accordance with the charge polarity applied to the biomolecule sample and the charge polarity applied to said conductive plates.

24. The BAS as specified in claim 7 further comprising an uncharged bead-antibody system in which altered targets of the antibody cause a permanent attachment of the uncharged bead-antibody at areas of study on the biomolecule.

25. The BAS as specified in claim 7 further comprising a hermetic vacuum input port that can extend from a surface of said input tube or said output tube, wherein to said vacuum port is attached a vacuum pump that creates a partial vacuum within said input tube, said output tube and said space between said anti-parallel cilium, wherein said partial vacuum reduces background noise and increases said resolution of said three-dimensional image.

26. The BAS as specified in claim 1 wherein said d-c power source is comprised of a rechargeable battery.

* * * * *